(12) United States Patent
Dwivedi et al.

(10) Patent No.: US 9,212,166 B2
(45) Date of Patent: Dec. 15, 2015

(54) PROCESS FOR THE PREPARATION OF DABIGATRAN ETEXILATE MESYLATE AND POLYMORPHS OF INTERMEDIATES THEREOF

(71) Applicant: CADILA HEALTHCARE LIMITED, Ahmedabad, Gujarat (IM)

(72) Inventors: Shriprakash Dhar Dwivedi, Gujarat (IN); Ramesh Chandra Singh, Gujarat (IN); Jigar Mukundbhai Raval, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 14/373,163

(22) PCT Filed: Jan. 21, 2013

(86) PCT No.: PCT/IN2013/000037
§ 371 (c)(1),
(2) Date: Nov. 25, 2014

(87) PCT Pub. No.: WO2013/111163
PCT Pub. Date: Aug. 1, 2013

(65) Prior Publication Data
US 2015/0011589 A1    Jan. 8, 2015

(30) Foreign Application Priority Data

Jan. 20, 2012 (IN) .......................... 210/MUM/2012
Mar. 22, 2012 (IN) .......................... 778/MUM/2012
May 14, 2012 (IN) ......................... 1462/MUM/2012

(51) Int. Cl.
*C07D 401/12* (2006.01)
*C07D 213/75* (2006.01)

(52) U.S. Cl.
CPC ............ *C07D 401/12* (2013.01); *C07D 213/75* (2013.01); *Y10T 428/2982* (2015.01)

(58) Field of Classification Search
CPC ..................................................... C07D 401/12
USPC ..................................................... 546/273.4
See application file for complete search history.

(56) References Cited

U.S. PATENT DOCUMENTS

| | | |
|---|---|---|
| 6,087,380 A | 7/2000 | Hauel et al. |
| 7,202,368 B2 | 4/2007 | Zerban et al. |
| 7,932,273 B2 | 4/2011 | Schmid et al. |
| 2006/0004064 A1 | 1/2006 | Zerban et al. |
| 2008/0119523 A1 | 5/2008 | Schmid et al. |

FOREIGN PATENT DOCUMENTS

| | | |
|---|---|---|
| WO | 98/37075 A1 | 8/1998 |
| WO | 03/074056 A1 | 9/2003 |
| WO | 2006/131491 A1 | 12/2006 |
| WO | 2007/071742 A1 | 6/2007 |
| WO | 2008/059029 A2 | 5/2008 |
| WO | 2009/153214 A1 | 12/2009 |
| WO | 2012/004396 A2 | 1/2012 |

OTHER PUBLICATIONS

Norbert H. Hauel, et al.: "Structure-Based Design of Novel Potent Nonpepti De Thrombin Inhibitors"; Journal of Medicinal Chemi Stry. American Chemical Society. US. vol. 45. No. 9. Mar. 26, 2002; pp. 1757-1766. XP001098844. ISSN: 0022-2623. DOI: 10.1021/JM0109513 Schemes 4 and 5. Compounds 29d, 30 And 31; Table 2 p. 1764. col. 2. Paragraph 2 p. 1765. col. 1. Paragraphs 2.3.5.

*Primary Examiner* — Patricia L Morris
(74) *Attorney, Agent, or Firm* — Ladas & Parry LLP

(57) ABSTRACT

The present invention provides crystalline form of intermediates of Formula 2A,

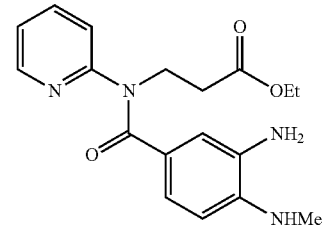

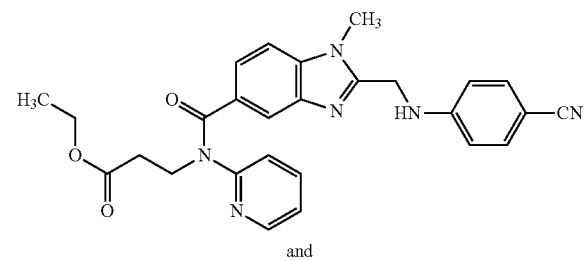

and

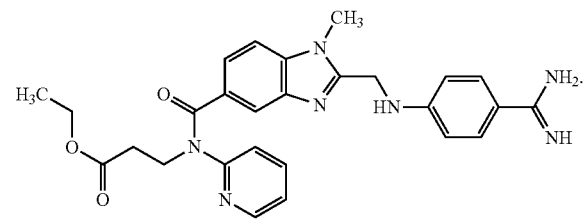

The present invention also provides process for the preparation of dabigatran etexilate mesylate; polymorph of intermediates thereof; particularly processes for the preparation of crystalline form of intermediates. The present invention also relates to the use of crystalline intermediates for the preparation of dabigatran etexilate mesylate.

14 Claims, 5 Drawing Sheets

Figure 1:
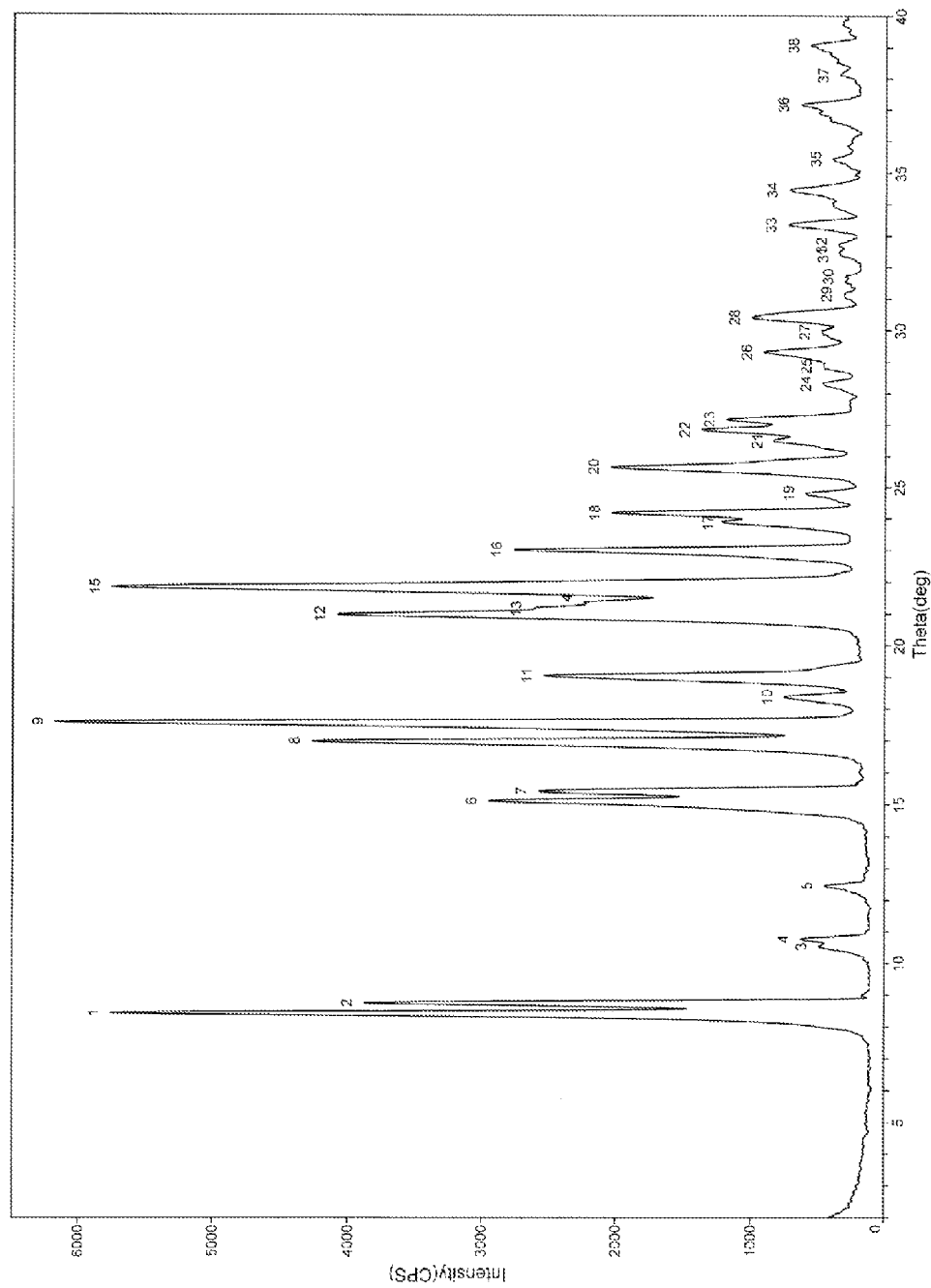

PROCESS FOR THE PREPARATION OF DABIGATRAN ETEXILATE MESYLATE AND POLYMORPHS OF INTERMEDIATES THEREOF

RELATED APPLICATION INFORMATION

This application is a 371 of International Application PCT/IN2013/000037 filed 21 Jan. 2013 entitled "Process for the Preparation of Dabigatran Etexilate Mesylate and Polymorphs of Intermediates Thereof", which was published in the English language on 1 Aug. 2013, with International Publication Number WO 2013/111163 A2 and which claims priority from Indian Patent Applications Numbers 210/MUM/2012 filed 20 Jan. 2012, 778/MUM/2012 filed 22 Mar. 2012 and 1462/MUM/2012 filed 14 May 2012, the content of which is incorporated herein by reference.

FIELD OF THE INVENTION

The present invention relates to process for the preparation of dabigatran etexilate mesylate and polymorph of intermediates thereof. In particular, the present invention relates to crystalline form of intermediates of Formula 2A, Formula 2B and Formula E. More particular, the present invention relates to processes for the preparation of crystalline form of intermediates. Further, the invention also relates to the use of crystalline intermediates for the preparation of dabigatran etexilate mesylate.

BACKGROUND OF THE INVENTION

Dabigatran etexilate and the tautomers, racemates, enantiomers, pharmacologically acceptable acid addition salts, solvates, hydrates and prodrugs thereof, particularly its acid addition salt with methanesulfonic acid being represented as compound of Formula (I).

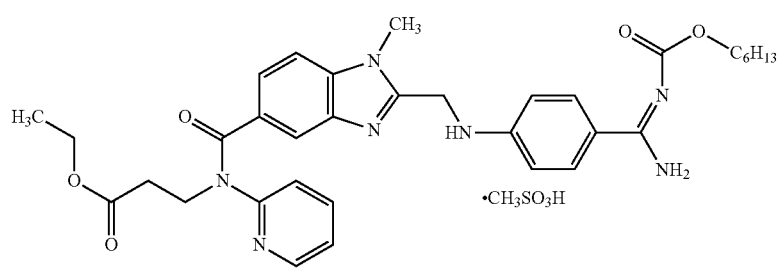

(I)

The active compound dabigatran etexilate is known from international (PCT) publication WO 98/37075, wherein compounds with a thrombin-inhibiting and thrombin time prolonging activity are disclosed, under the name 1-methyl-2-[N-[4-(N-hexyloxycarbonylamidino)phenyl]-aminomethyl]-benzimidazol-5-yl-carboxylic acid-N-(2-pyridyl)-N-(2-ethoxycarbonylethyl)mide also known as BIBR 1048. The compound of Formula (I) is a double prodrug of the compound (E').

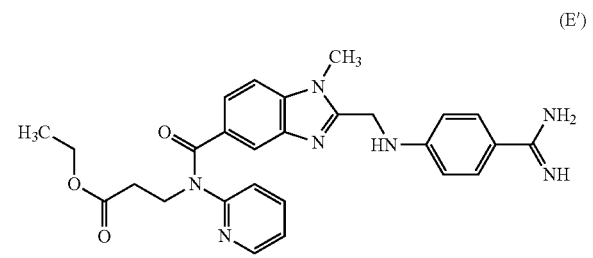 [SMILES: CCOC(=O)CCN(C(=O)c1ccc2c(c1)nc(CNc1ccc(C(=N)N)cc1)n2C)c1ccccn1]

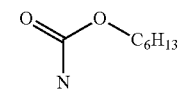

(E')

Therefore, the compound of Formula (I) i.e. dabigatran etexilate mesylate is only converted into the active compound, namely the compound of Formula (E'), after entering the body. The main indication for the compound of chemical Formula (I) is the post-operative prevention of deep vein thrombosis and the prevention of strokes.

International (PCT) Publication WO 98/37075 discloses the process for the preparation of substituted (4-benzimidazol-2-ylmethylamino)benzamidines by reacting the corresponding, substituted (4-benzimidazol-2-ylmethylamino) benzonitriles with ammonia, i.e. the process for the preparation of dabigatran etexilate. This method is very tedious in terms of production costs and results in a high load of acids requiring disposal.

International (PCT) Publication WO 03/074056 A1 discloses acid addition salt of dabigatran etexilate with methanesulfonic acid.

U.S. Pat. No. 7,932,273 B2 discloses three polymorphic forms viz. Form I, Form II and hemihydrate forms of dabigatran etexilate mesylate characterized by x-ray powder diffraction and differential scanning calorimetry.

International (PCT) publication WO 2006/131491 discloses different polymorphic forms of 3-[(2-{[4-(hexyloxycarbonylamino-imino-methyl)-phenylamino]-methyl}-1-methyl-1H-benzimidazole-5-carbonyl)-pyridin-2-yl-amino]-propionate i.e. dabigatran etexilate free base. In particular, the WO '491 discloses anhydrous Form I, anhydrous Form II and a tetrahydrate Form.

International (PCT) publication WO 2008/059029 A2 discloses anhydrous Form III, anhydrous Form IV, monohydrate Form I, monohydrate Form II, as well as nitrobenzene solvate of dabigatran etexilate free base.

U.S. Pat. No. 7,202,368 B2 discloses the process for preparing dabigartan etexilate. The process disclosed in the art involves cumbersome steps of column chromatography and the obtained intermediates are in residue form which results in low purity and yield of the product.

In view of the above, it is therefore, desirable to provide an efficient, economical and eco-friendly process for the preparation of dabigatran etexilate mesylate. In particular, the present inventors have found novel crystalline form of intermediates of Formula 2A, Formula 2B and Formula E having good physiochemical properties and useful for further processing.

Therefore, the present invention provides novel crystalline form of intermediates of dabigatran etexilate. In particular, the present invention provides crystalline form of compound ethyl 3-(3-amino-4-(methylamino)-N-(pyridin-2-yl)benzamido)propanoate of Formula 2A, ethyl 3-(2-((4-cyanophenylamino)methyl)-1-methyl-N-(pyridin-2-yl)-1H-benzo[d]imidazole-5-carboxamido) propanoate, of Formula 2B and 1-methyl-2-[N-(4-amidinophenyl)aminomethyl]benzimidazol-5-yl-carboxylic acid-N-phenyl-N-(2-ethoxycarbonylethyl)amide hydrochloride of Formula (E) as well as its process of their preparation and use thereof for the preparation of dabigatran etexilate mesylate.

SUMMARY OF THE INVENTION

In one general aspect, the present invention relates to a crystalline form of ethyl 3-(3-amino-4-(methylamino)-N-(pyridin-2-yl)benzamido)propanoate of Formula (2A).

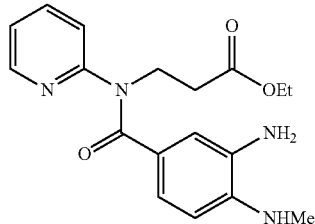

(2A)

In another general aspect, the present invention relates to a crystalline form of ethyl 3-(2-((4-cyanophenylamino)methyl)-1-methyl-N-(pyridin-2-yl)-1H-benzo[d]imidazole-5-carboxamido) propanoate of Formula (2B).

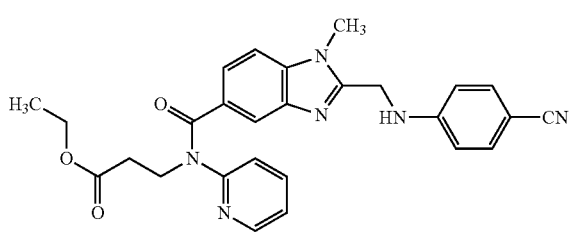

(2B)

In another general aspect, the present invention relates to a process for preparing crystalline form of 1-methyl-2-[N-(4-amidinophenyl)aminomethyl]benzimidazol-5-yl-carboxylic acid-N-phenyl-N-(2-ethoxycarbonylethyl)amide hydrochloride of Formula (E).

In another general aspect, the present invention relates to use of crystalline form of compound of Formula (2A), Formula (2B) and Formula (E), respectively for the preparation of dabigatran etexilate of Formula (I).

In another general aspect, the present invention relates to an amorphous form of dabigatran etexilate of Formula (F) and process for its preparation.

In another general aspect, the present invention relates to crystalline dabigatran etexilate mesylate of Formula (I) having particle size distribution with about 90% of particles (D 90) being ≤200 microns, 50% of particles (D50) being ≤150 microns; 10% of particles (D10) being ≤100 microns or any combination thereof.

In another general aspect, the invention provides an improved process for preparing crystalline Form-I of dabigatran etexilate mesylate of Formula (I).

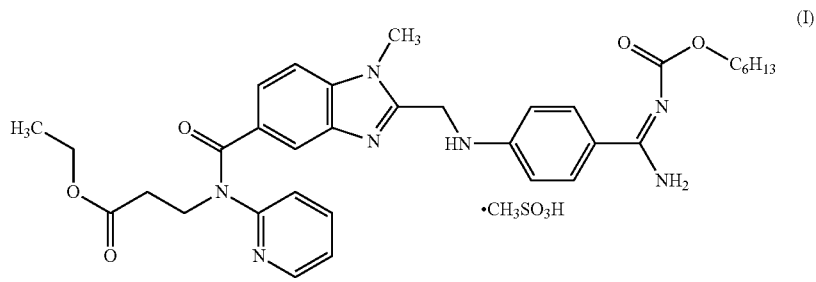

(I)

The present invention also relates to the process of preparation of the crystalline forms of intermediates of Formula (2A) and Formula (2B), respectively.

In another general aspect, the present invention relates to a crystalline form of 1-methyl-2-[N-(4-amidinophenyl)aminomethyl]benzimidazol-5-yl-carboxylic acid-N-phenyl-N-(2-ethoxy carbonyl ethyl)amide hydrochloride of Formula (E)

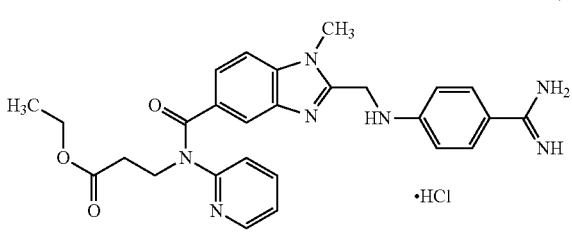

(E)

the process comprising:
(a) reacting 4-chloro-3-nitrobenzoic acid with monomethyl amine to obtain 4-(methylamino)-3-nitrobenzoic acid of Formula (A);
(b) reacting 4-(methylamino)-3-nitrobenzoic acid of Formula (A) with ethyl 3-(pyridin-2-ylamino) propanoate of Formula (B) in halogenating agent to obtain ethyl 3-(4-(methylamino)-3-nitro-N-(pyridin-2-yl)benzamido)propanoate of Formula (C);
(c) reducing ethyl 3-(4-(methylamino)-3-nitro-N-(pyridin-2-yl)benzamido)propanoate of Formula (C) in-situ with a suitable reducing agent in suitable organic solvent to obtain ethyl 3-(3-amino-4-(methylamino)-N-(pyridin-2-yl)benzamido)propanoate of Formula (2A);
(d) reacting ethyl 3-(3-amino-4-(methylamino)-N-(pyridin-2-yl)benzamido)propanoate of Formula (2A) with 2-(4-cyanophenylamino)acetic acid of Formula (D) in presence of coupling agent to obtain ethyl 3-(2-((4-cyanophenylamino)methyl)-1-methyl-N-(pyridin-2-yl)-1H-benzo[d]-imidazole-5-carboxamido) propanoate of Formula (2B);

(e) reacting ethyl 3-(2-((4-cyanophenylamino)methyl)-1-methyl-N-(pyridin-2-yl)-1H-benzo[d]imidazole-5-carboxamido) propanoate of Formula (2B) with an acid in a suitable organic solvent to obtain reaction mixture and basifying the reaction mixture to obtain ethyl 3-(2((4-carbamimidoylphenylamino)methyl)-1-methyl-N-(pyridin-2-yl)-1H-benzo[d]imidazole-5-carboxamido)propanoate hydrochloride of Formula (E);

(f) reacting 3-(2-((4-carbamimidoylphenylamino)methyl)-1-methyl-N-(pyridin-2-yl)-1H-benzo[d]imidazole-5-carboxamido)propanoate hydrochloride of Formula (E) with n-hexyl chloroformate in presence of base in suitable organic solvent to obtain dabigatran etexilate of Formula (F); and (g) reacting dabigatran etexilate of Formula (F) with methane sulfonic acid in a suitable organic solvent to obtain dabigatran etexilate mesylate of Formula (I).

In another general aspect, the invention relates to dabigatran etexilate mesylate Formula (I) having total purity of about 99% or more, particularly about 99.5% or more, more particularly about 99.9%, when measured by area percentage of HPLC.

BRIEF DESCRIPTION OF THE ACCOMPANYING DRAWINGS

FIG. 1 discloses the x-ray diffractogram of crystalline ethyl 3-(3-amino-4-(methylamino)-N-(pyridin-2-yl)benzamido) propanoate of Formula (2A).

Figure 2:
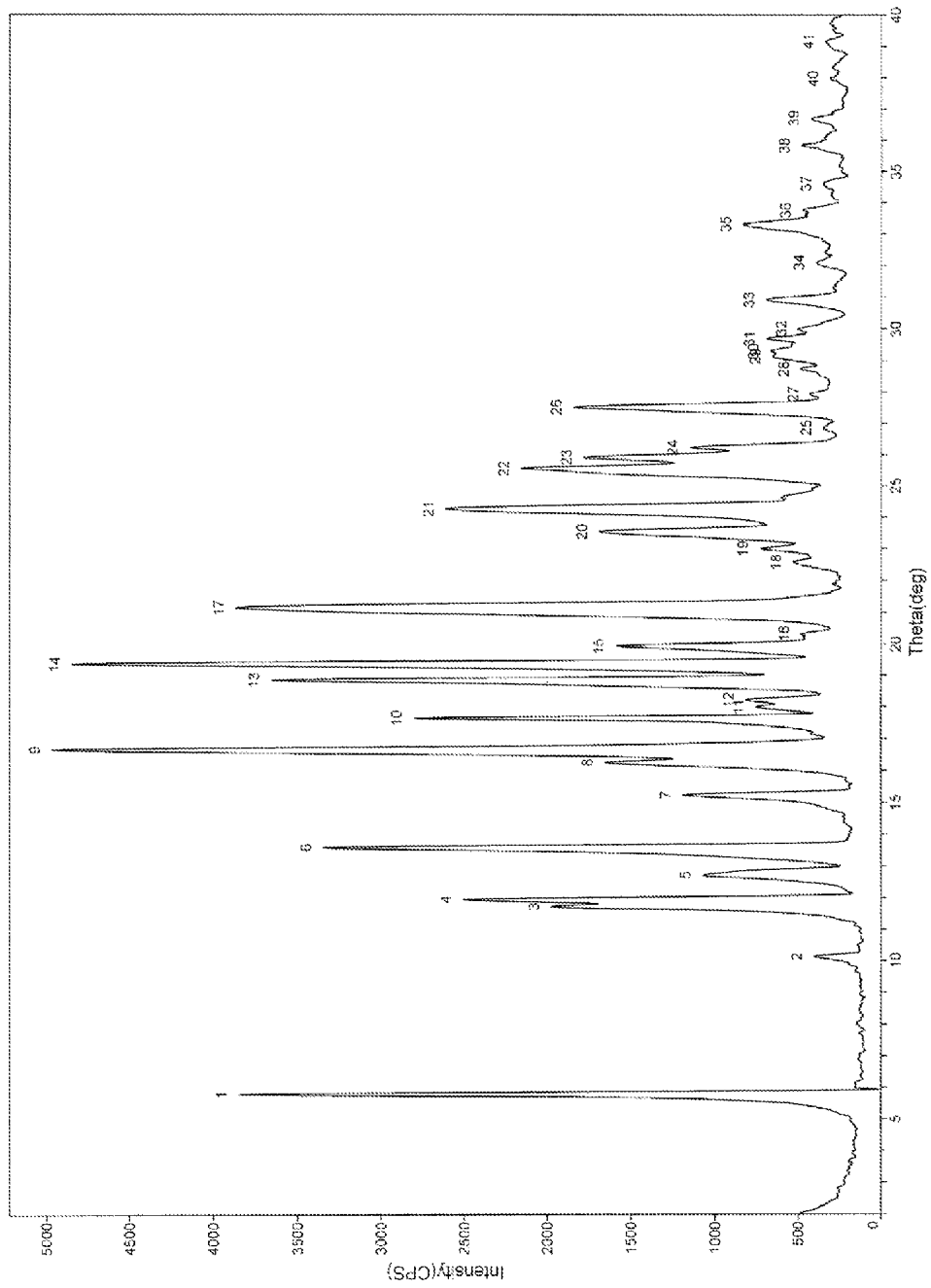

FIG. 2 discloses the x-ray diffractogram of crystalline ethyl 3-(2-((4-cyanophenylamino)methyl)-1-methyl-N-(pyridin-2-yl)-1H-benzo[d]imidazole-5-carboxamido)propanoate of Formula (2B).

Figure 3:
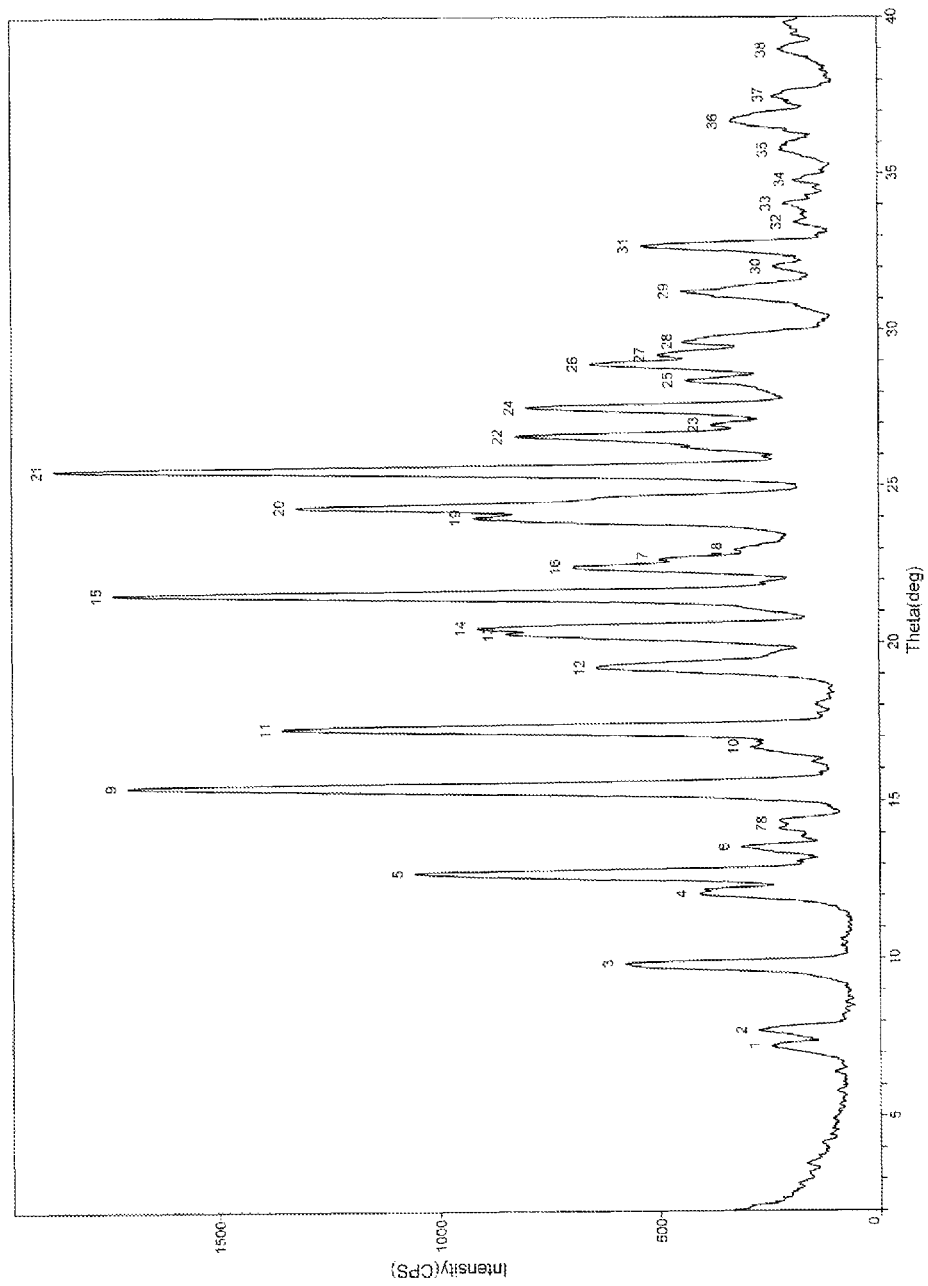

FIG. 3 discloses the x-ray diffractogram of crystalline 1-methyl-2-[N-(4-amidinophenyl)amino methyl]benzimidazol-5-yl-carboxylic acid-N-phenyl-N-(2-ethoxycarbonyl-ethyl)amide hydrochloride of Formula (E).

Figure 4:
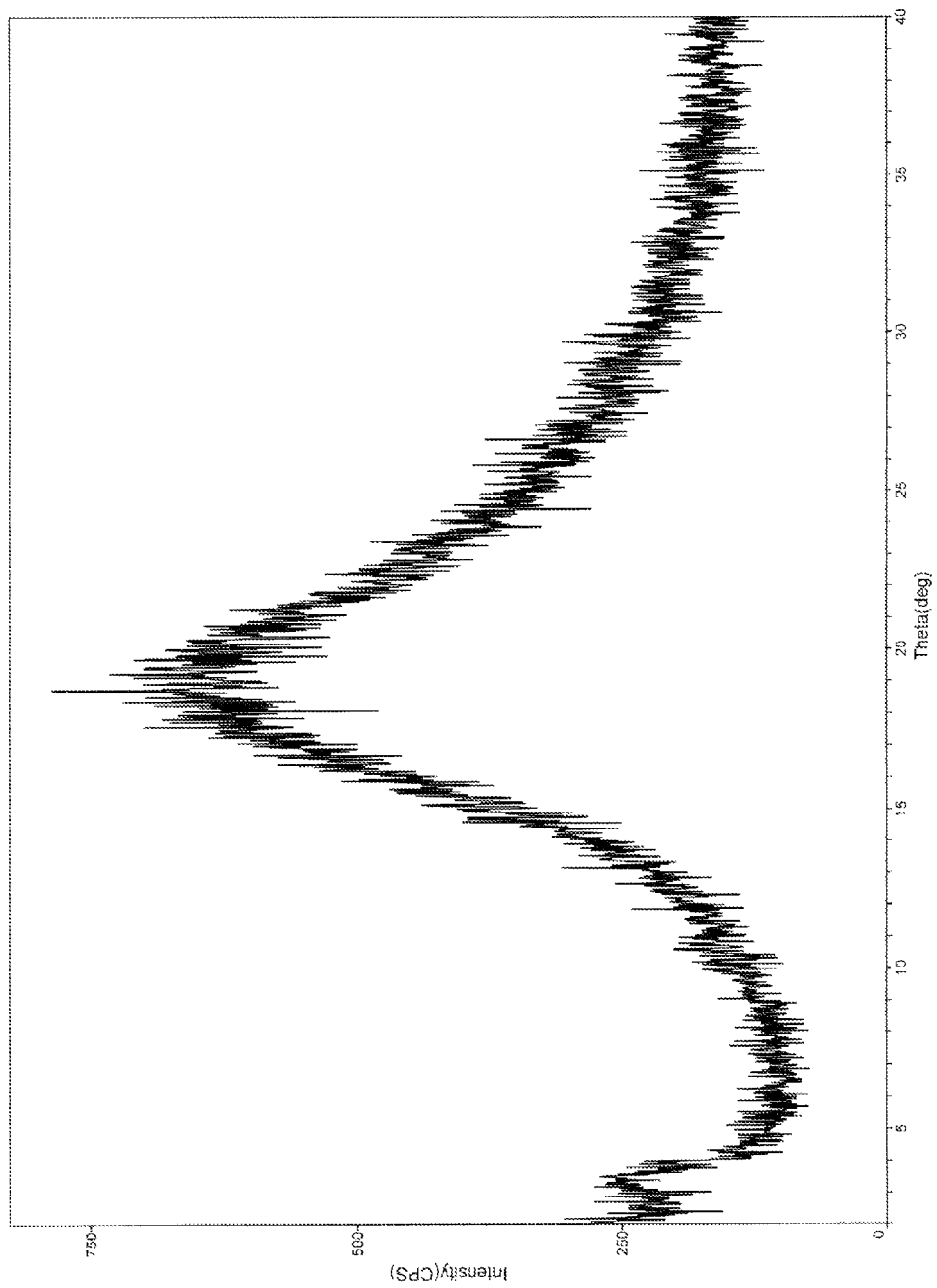

FIG. 4 discloses the x-ray diffractogram (XRD) of amorphous form of dabigatran etexilate of Formula (F).

Figure 5:
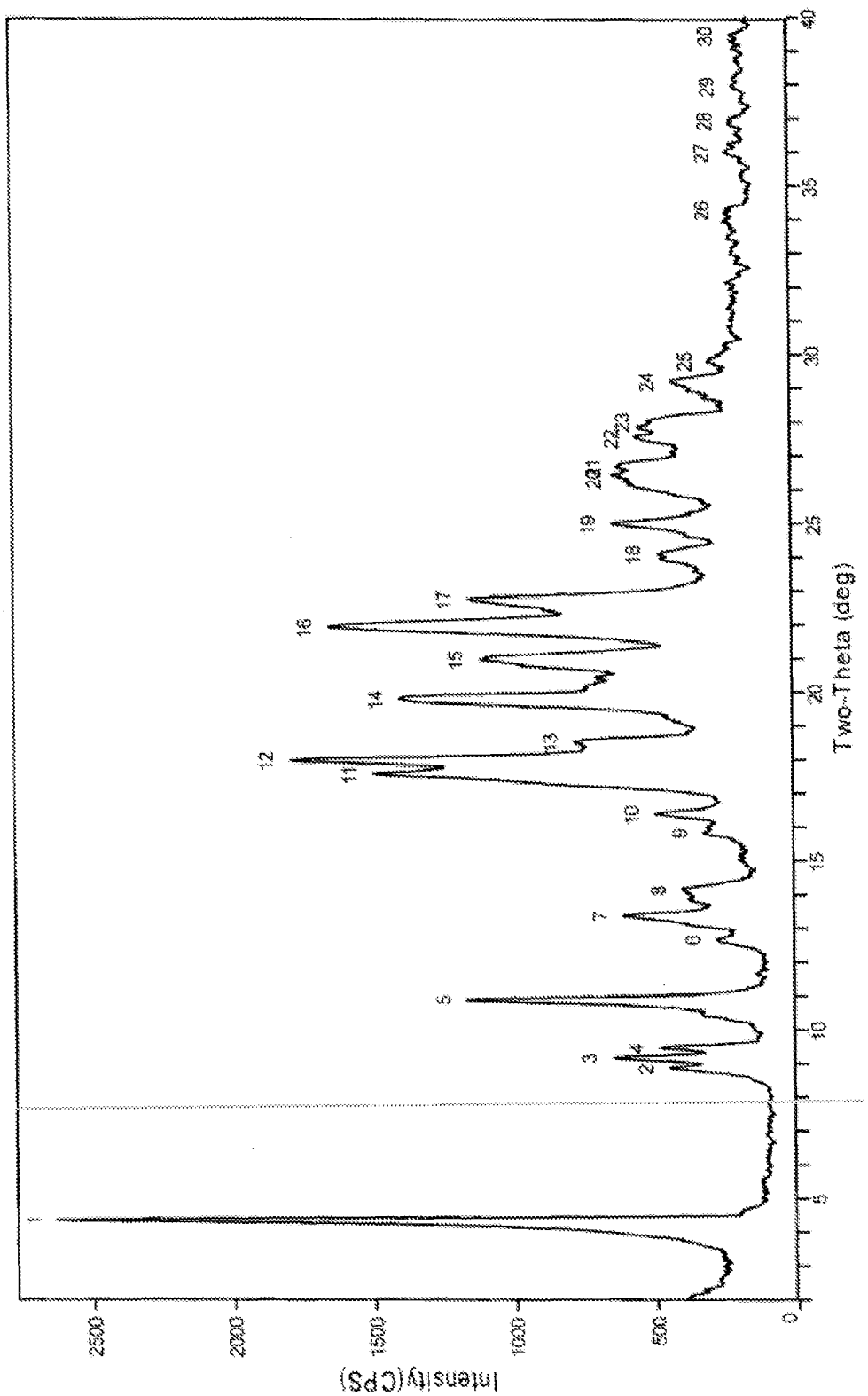

FIG. 5 discloses the x-ray diffractogram (XRD) of crystalline Form-I of dabigatran etexilate mesylate of Formula (I).

DETAILED DESCRIPTION OF THE INVENTION

The inventors of the present invention have discovered novel crystalline form of intermediates of Formula (2A) and (2B) which are key intermediates for dabigatran etexilate of Formula (F) or its mesylate salt of Formula (I). Further, the inventors have also discovered the novel crystalline form of 1-methyl-2-[N-(4-amidinophenyl)amino methyl]benzimidazol-5-yl-carboxylic acid-N-phenyl-N-(2-ethoxycarbonyl ethyl)amide hydrochloride of Formula (E), which is key intermediate for dabigatran etexilate.

The purity of dabigatran etexilate depends on the purity of compound of Formula (E). Therefore, the novel crystalline form of compound of Formula (E) with better physiochemical properties and purity provides substantially pure dabigatran etexilate of Formula (F) or its mesylate salt of Formula (I).

All ranges recited herein include the endpoints, including those that recited a range "between" two values. Terms such as "about", "general", "substantially" and the like are to be construed as modifying a term or value such that it is not an absolute. Such terms will be defined by the circumstances and the terms that they modify as those terms are understood by those skill in the art. This includes, at the very least, a degree of expected experimental error, technique error and instrument error for a given technique used to measure a value.

The term "crystallizing" herein means heating a "slurry" or "suspension" or "solution" of compound from about 25° C. to about 10° C. above or below of the reflux temperature of solvent, and optionally cooling to the ambient temperature to obtain crystalline form of compound. The term "ambient temperature" herein means temperature of about 20° C. or less.

When a molecule or other material is identified herein as "substantially pure", it generally means, unless specified otherwise, that the material is about 99% pure or more. In general, this refers to purity with regard to unwanted residual solvents, reaction byproducts, impurities and unreacted staring materials.

As used here in the term "obtaining" may include filtration, filtration under vacuum, centrifugation, and decantation to isolate product. The product obtained may be further or additionally dried to achieve the desired moisture values. For example, the product may be dried in a hot air oven, tray drier, dried under vacuum and/or in a Fluid Bed Drier.

"Suitable solvent" means a single or a combination of two or more solvents.

In one general aspect, the present invention relates to a crystalline form of ethyl 3-(3-amino-4-(methylamino)-N-(pyridin-2-yl)benzamido)propanoate of Formula (2A).

(2A)

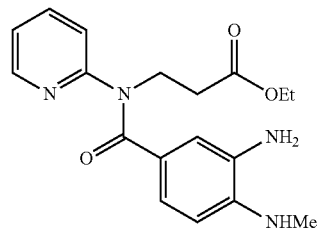

The crystalline form of compound of Formula (2A) is characterized by the x-ray diffraction pattern that exhibits the characteristic peaks at 8.4°, 8.7°, 15.1°, 15.4°, 16.9°, 17.5°, 19.0°, 20.9°, 21.8°, 23.0°, 24.1°, 25.6°±0.2° 2θ. The crystalline form of compound of Formula (2A) may further be characterized by x-ray powder diffraction pattern substantially as depicted in FIG. 1.

In another general aspect, the present invention relates to a process for the preparation of crystalline ethyl 3-(3-amino-4-(methylamino)-N-(pyridin-2-yl)benzamido)propanoate of Formula (2A), the process comprising the steps of:

(a) reacting 4-(methylamino)-3-nitrobenzoic acid of Formula (A) with ethyl 3-(pyridin-2-ylamino)propanoate (B) in halogenating agent to obtain ethyl 3-(4-(methylamino)-3-nitro-N-(pyridin-2-yl)benzamido)propanoate (C);

(b) reducing ethyl 3-(4-(methylamino)-3-nitro-N-(pyridin-2-yl)benzamido)propanoate (C) in-situ in suitable organic solvent in presence of suitable reducing agent;

(c) optionally, isolating ethyl 3-(3-amino-4-(methylamino)-N-(pyridin-2-yl)benzamido)propanoate of Formula (2A); and (d) crystallizing ethyl 3-(3-amino-4-(methylamino)-N-(pyridin-2-yl)benzamido)propanoate of Formula (2A).

In general, the halogenating agent comprises of thionyl chloride, phosphorous trichloride, phosphorous pentachloride, phosphorus oxychloride and the like. In particular, thionyl chloride may be used. The reaction may be performed in presence of catalytic amount of dimethylformamide.

The embodiments of the process further includes reduction of ethyl 3-(4-(methylamino)-3-nitro-N-(pyridin-2-yl)benzamido)propanoate (C) in-situ with suitable reducing agent. The suitable reducing agent comprises of Sn/HCl, Fe/HCl, Na$_2$Sx, sodium borohydride, lithium aluminium hydride, Raney nickel, Pd/C, Pt/C and optionally a mixture of either of them. In particular, Pd/C may be used.

In general, the suitable organic solvent in step (b) comprises one or more of methanol, ethanol, isopropanol, butanol, acetone, methyl isobutyl ketone, ethyl acetate, butyl acetate, isopropyl acetate, tetrahydrofuran, 2-methyltetrahydrofuran, or mixtures thereof. In particular, the suitable solvent may be ethyl acetate.

The embodiments of the process further includes removal of ethyl acetate to obtain ethyl 3-(3-amino-4-(methylamino)-N-(pyridin-2-yl)benzamido)propanoate of Formula (2A). The compound of Formula (2A) as residue or an isolated compound may further be crystallized to obtain crystalline ethyl 3-(3-amino-4-(methylamino)-N-(pyridin-2-yl)benzamido)propanoate of Formula (2A). The suitable solvent for crystallization comprises one or more of methanol, ethanol, isopropanol, butanol, acetone, methyl isobutyl ketone, toluene, xylene, methylene dichloride, ethylene dichloride and the like. In particular, isopropanol or toluene may be used.

The crystalline ethyl 3-(3-amino-4-(methylamino)-N-(pyridin-2yl)benzamido) propanoate of Formula (2A) obtained may be characterized by x-ray powder diffraction pattern substantially as depicted in FIG. 1 and 2θ values as disclosed herein above.

In another general aspect, the present invention relates to a crystalline form of an ethyl 3-(2-((4-cyanophenylamino)methyl)-1-methyl-N-(pyridin-2-yl)-1H-benzo[d]imidazole-5-carboxamido) propanoate of Formula (2B).

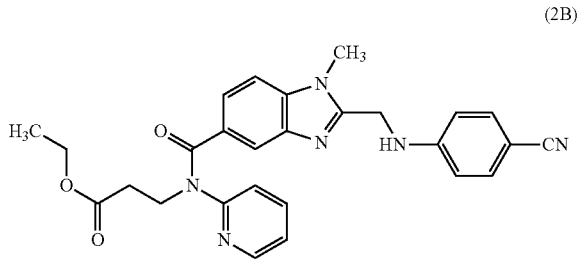 [SMILES: CCOC(=O)CCN(C(=O)c1ccc2c(c1)nc(CNc1ccc(C#N)cc1)n2C)c1ccccn1]

(2B)

The crystalline form of compound of Formula (2B) is characterized by the x-ray diffraction pattern that exhibits the characteristic peaks at 5.8°, 11.7°, 11.9°, 13.5°, 16.6°, 17.6°, 18.8°, 19.3°, 21.1°, 24.2°, 25.5°, 25.9°, 27.5° 2θ±0.2. The crystalline form of compound of Formula (2B) may further be characterized by x-ray powder diffraction pattern substantially as depicted in FIG. 2.

In another general aspect, the present invention relates to a process of preparation of crystalline ethyl 3-(2-((4-cyanophenylamino)methyl)-1-methyl-N-(pyridin-2-yl)-1H-benzo[d]imidazole-5-carboxamido)propanoate of Formula (2B),

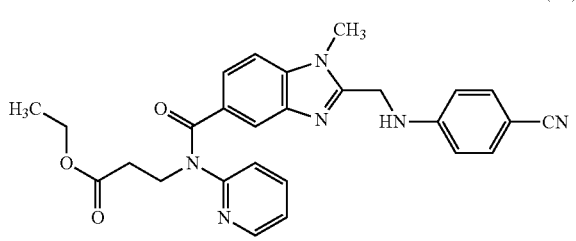

(2B)

the process comprising:
(a) reacting ethyl 3-(3-amino-4-(methylamino)-N-(pyridin-2-yl)benzamido)propanoate of Formula (2A) with 2-(4-cyanophenylamino)acetic acid of Formula (D) in presence of coupling reagent in first organic solvent to obtain compound of Formula (2B);

(b) removing the first organic solvent to obtain ethyl 3-(2-((4-cyanophenylamino)methyl)-1-methyl-N-(pyridin-2-yl)-1H-benzo[d]imidazole-5-carboxamido)propanoate of Formula (2B) as residue;

(c) treating the residue with second organic solvent or mixture thereof with water;

(d) removing the second organic solvent; and (e) crystallizing ethyl 3-(2-((4-cyanophenylamino)methyl)-1-methyl-N-(pyridin-2-yl)-1H-benzo[d]imidazole-5-carboxamido)propanoate of Formula (2B).

In general, the coupling reagent may be a functional group transforming reactant generally employed in the organic synthesis to convert alcohols, amines and nitriles into carbamates, esters, and urea derivatives. In particular, the coupling agent comprises one or more of 1,1'-carbonyldiimidazole (CDI), N,N'-dicyclohexylcarbodiimide (DCC), 1-ethyl-3-(3-dimethyllaminopropyl)carbodiimide hydrochloride (EDC.HCl), polyphosphoric acid (PPA), mesylchloride, thionyl chloride and the like. Most particularly, 1,1'-Carbonyldiimidazole (CDI) may be used.

In general, the first organic solvent comprises one or more of ethyl acetate, isopropyl acetate, butyl acetate, toluene, xylene, ethyl benzene, methylene dichloride, ethylene dichloride, chlorobenzene, chloroform, cyclohexane, tetrahydrofuran, 2-methyltetrahydrofuran, acetonitrile and the like. In particular, toluene or xylene may be used.

The second organic solvent comprises one or more of ethyl acetate, isopropyl acetate, butyl acetate, methylene dichloride, ethylene dichloride, chlorobenzene, chloroform, cyclohexane, n-hexane, n-heptane, tetrahydrofuran, 2-methyltetrahydrofuran, acetonitrile and the like. In particular, methylene dichloride may be used.

The embodiments of the process includes reacting compound of Formula (D) with compound of Formula (2A) in presence of CDI in toluene at 60° C. for about 3 hours. The reaction mixture was heated to 100° C. for about 3 hours. The first solvent toluene was removed by distillation under vacuum followed by treatment with second organic solvent methylene dichloride. The reaction mixture may be washed with water followed by removal of second organic solvent to obtain residue.

The residue obtained may be crystallized in one or more of suitable organic solvent comprises of methanol, ethanol, isopropanol, butanol, acetone, methyl ethyl ketone, methyl isobutyl ketone, ethyl acetate, isopropyl acetate, butyl acetate, acetonitrile, N-methylpyrrolidine; dimethylformamide, dimethylacetamide and the like. In particular, ethyl acetate or butyl acetate may be used. The residue may optionally be heated in ethyl acetate or butyl acetate and cooled to obtain crystalline form of compound of Formula (2B).

The crystalline compound (2B) obtained may be characterized by x-ray powder diffraction pattern substantially as depicted in FIG. 2 and 2θ values disclosed herein above.

In another general aspect, the present invention relates to a crystalline form of 1-methyl-2-[N-(4-amidinophenyl)aminomethyl]benzimidazol-5-yl-carboxylic acid-N-phenyl-N-(2-ethoxy carbonyl ethyl)amide hydrochloride of Formula (E),

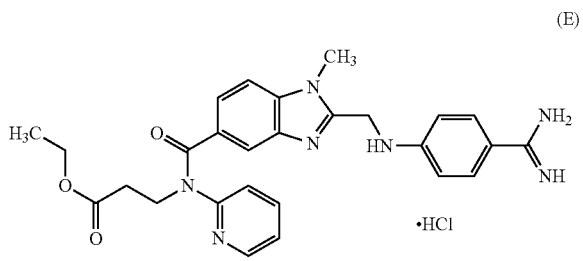 [SMILES: CCOC(=O)CCN(C(=O)c1ccc2c(c1)nc(CNc1ccc(C(=N)N)cc1)n2C)c1ccccn1 ; Cl]

The crystalline form of compound of Formula (E) is characterized by the x-ray diffraction pattern that exhibits the characteristic peaks at 7.1°, 7.7°, 9.7°, 12.0°, 13.5°, 14.3°, 15.4°, 17.2°, 19.2°, 20.4°, 21.5°, 22.3°, 23.9°, 24.3°, 25.4°, 26.5°, 27.4°, 28.8°±0.2 2θ. The crystalline form of compound of Formula (E) may be further characterized by x-ray powder diffraction pattern substantially as depicted in FIG. 3.

In another general aspect, the present invention relates to a process for preparation of crystalline form of 1-methyl-2-[N-(4-amidinophenyl)aminomethyl]benzimidazol-5-yl-carboxylic acid-N-phenyl-N-(2-ethoxycarbonylethyl)amide hydrochloride of Formula (E),

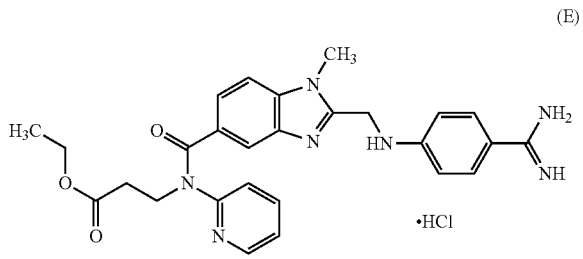 [SMILES: CCOC(=O)CCN(C(=O)c1ccc2c(c1)nc(CNc1ccc(C(=N)N)cc1)n2C)c1ccccn1 ; Cl]

the process comprising:
(a) providing 1-methyl-2-[N-(4-amidinophenyl)aminomethyl]benzimidazol-5-yl-carboxylic acid-N-phenyl-N-(2-ethoxycarbonylethyl)amide hydrochloride of Formula (E) solution in one or more of suitable organic solvent; and
(b) obtaining crystalline form of compound of Formula (E) by removal of solvent.

In general, the suitable organic solvent comprises one or more of methanol, ethanol, isopropanol, n-butanol, t-butanol, acetone, methyl ethyl ketone, diethyl ether, diisopropyl ether, methyl tert-butyl ether, ethyl acetate, isopropyl acetate, butyl acetate, dimethylformamide, dimethylacetamide, N-methylpyrrolidine, toluene, xylene, acetonitrile or a mixture thereof. In particular t-butanol may be used.

In another general aspect, the present invention provides use of crystalline form of compound of Formula (2A), Formula (2B) and Formula (E) for the preparation of dabigatran etexilate of Formula (I).

In another general aspect, the present invention relates to a process for preparation of dabigatran etexilate of Formula (F) or its pharmaceutically acceptable salts thereof, the process comprising:
(a) treating ethyl 3-(2-((4-cyanophenyl amino)methyl)-1-methyl-N-(pyridin-2-yl)-1H-benzo[d]imidazole-5-carboxamido)propanoate of Formula (2B) with an acid in suitable organic solvent to obtain reaction mixture;
(b) basifying the reaction mixture followed by removal of solvent to obtain residue;
(c) crystallizing the residue in suitable organic solvent to obtain crystalline 1-methyl-2-[N-(4-amidinophenyl)aminomethyl]benzimidazol-5-yl-carboxylic acid-N-phenyl-N-(2-ethoxycarbonyl ethyl)amide hydrochloride of Formula (E);
(d) reacting crystalline 1-methyl-2-[N-(4-amidinophenyl)aminomethyl]benzimidazol-5-yl-carboxylic acid-N-phenyl-N-(2-ethoxycarbonylethyl)amide hydrochloride of Formula (E) with n-hexyl chloroformate in presence of base in suitable organic solvent to obtain dabigatran etexilate of Formula (F);
(e) crystallizing dabigatran etexilate in suitable organic solvent; and
(f) obtaining substantially pure dabigatran etexilate of Formula (F) by removal of solvent;
(g) optionally, converting dabigatran etexilate of Formula (F) to its pharmaceutically acceptable salt thereof.

In general, the acid may be selected from organic or inorganic acid like formic acid, acetic acid, trifluoroacetic acid, hydrochloric acid, hydrobromic acid, sulfuric acid, phosphoric acid and the like. In particular hydrochloric acid may be used. The hydrochloric acid used may be aqueous hydrochloric acid, hydrochloric acid gas or solution of hydrochloric acid in a solvent like isopropanol, acetone, ethyl acetate and the like. In particular, hydrochloric acid gas may be used.

The suitable organic solvent in step (a) comprises one or more of methanol, ethanol, isopropanol, n-butanol, t-butanol, acetone, methyl ethyl ketone, diethyl ether, diisopropyl ether, methyl tert-butyl ether, ethyl acetate, isopropyl acetate, butyl acetate, dimethylformamide, dimethylacetamide, N-methylpyrrolidine, toluene, xylene, acetonitrile or a mixture thereof. In particular, ethanol may be used.

The reaction mixture may be basified with a base selected from ammonia, ammonium carbonate or ammonical solution in alcohols like methanol, ethanol, isopropanol, butanol and the like. In particular, ammonia may be used.

The solvent may be removed by the known techniques in the art like filtration, decantation, centrifugation, spray drying, evaporation and the like to obtain residue of 1-methyl-2-[N-(4-amidinophenyl)aminomethyl]benzimidazol-5-yl-carboxylic acid-N-phenyl-N-(2-ethoxycarbonyl ethyl)amide hydrochloride.

The residue of 1-methyl-2-[N-(4-amidinophenyl)aminomethyl]benzimidazol-5-yl-carboxylic acid-N-phenyl-N-(2-ethoxycarbonyl ethyl)amide hydrochloride may be crystallized by the methods described herein above to obtain crystalline form of compound (E).

In general, the crystalline 1-methyl-2-[N-(4-amidinophenyl)aminomethyl]benzimidazol-5-yl-carboxylic acid-N-phenyl-N-(2-ethoxycarbonyl ethyl)amide hydrochloride of

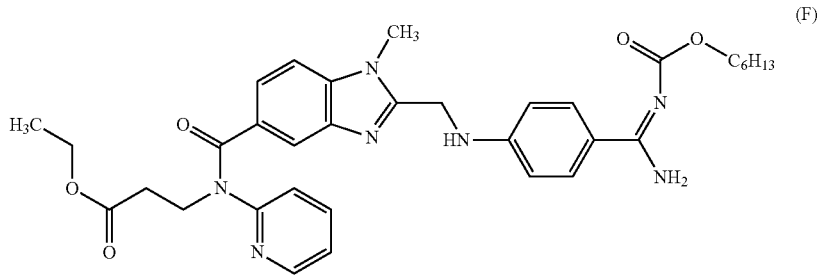

Formula (E) may be reacted with n-hexyl chloroformate in presence of suitable base. The suitable base may be selected from alkali or alkaline earth metal salts like sodium hydroxide, potassium hydroxide, lithium hydroxide, calcium hydroxide, sodium carbonate, potassium carbonate, sodium bicarbonate, potassium bicarbonate, sodium tert-butoxide, potassium tert-butoxide and the like. In particular, potassium carbonate may be used.

The reaction may be performed in suitable solvent comprises of one or more of methanol, ethanol, isopropanol, n-butanol, t-butanol, acetone, methyl ethyl ketone, ethyl acetate, isopropyl acetate, butyl acetate, dimethylformamide, dimethylacetamide, N-methylpyrrolidine, dimethylsulfoxide, toluene, xylene, acetonitrile or a mixture thereof with water. In particular, acetone-water mixture may be used to obtain dabigatran etexilate of Formula (F).

The dabigatran etexilate of Formula (F) thus obtained may be crystallized in suitable organic solvent by the known methods described herein above. The suitable solvent comprises one or more of methanol, ethanol, isopropanol, n-butanol, t-butanol, acetone, methyl ethyl ketone, ethyl acetate, isopropyl acetate, butyl acetate, dimethylformamide, dimethylacetamide, N-methylpyrrolidine, dimethylsulfoxide, toluene, xylene, acetonitrile or a mixture thereof. In particular, ethyl acetate may be used.

The embodiments of the process include isolation of substantially pure dabigatran etexilate of Formula (F) by removal of solvent. The solvent may be removed by the known techniques as described herein above. The substantially pure dabigatran etexilate of Formula (F) may optionally be converted to its pharmaceutically acceptable salts thereof.

The suitable pharmaceutically acceptable salt may be selected from hydrochloride, hydrobromide, oxalate, succinate, tartrate, mesylate, besylate and the like. In particulate, mesylate may be prepared.

In another general aspect, the invention provides an improved process for preparing dabigatran etexilate mesylate of Formula (I).

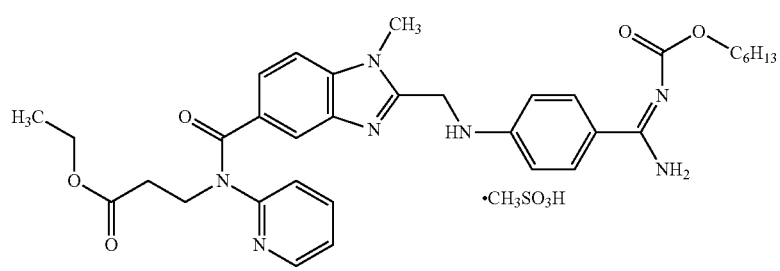

comprising the steps of:
(a) reacting 4-chloro-3-nitrobenzoic acid with monomethyl amine to obtain 4-(methylamino)-3-nitrobenzoic acid of Formula (A);
(b) reacting 4-(methylamino)-3-nitrobenzoic acid of Formula (A) with ethyl 3-(pyridin-2-ylamino) propanoate of Formula (B) in halogenating agent to obtain ethyl 3-(4-(methylamino)-3-nitro-N-(pyridin-2-yl)benzamido)propanoate of Formula (C);
(c) reducing ethyl 3-(4-(methylamino)-3-nitro-N-(pyridin-2-yl)benzamido)propanoate of Formula (C) in-situ with a suitable reducing agent in suitable organic solvent to obtain ethyl 3-(3-amino-4-(methylamino)-N-(pyridin-2-yl)benzamido)propanoate of Formula (2A);
(d) reacting ethyl 3-(3-amino-4-(methylamino)-N-(pyridin-2-yl)benzamido)propanoate of Formula (2A) with 2-(4-cyanophenylamino)acetic acid of Formula (D) in presence of coupling reagent in to obtain compound of Formula (2B);
(e) reacting ethyl 3-(2-((4-cyanophenylamino)methyl)-1-methyl-N-(pyridin-2-yl)-1H-benzo[d]imidazole-5-carboxamido) propanoate of Formula (2B) with an acid in a suitable organic solvent to obtain reaction mixture and basifying the reaction mixture to obtain ethyl 3-(2-((4-carbamimidoylphenylamino)methyl)-1-methyl-N-(pyridin-2-yl)-1H-benzo[d]imidazole-5-carboxamido)propanoate hydrochloride of Formula (E);
(f) reacting 3-(2-((4-carbamimidoylphenylamino)methyl)-1-methyl-N-(pyridin-2-yl)-1H-benzo[d]imidazole-5-carboxamido)propanoate hydrochloride of Formula (E) with n-hexyl chloroformate in presence of base in suitable organic solvent to obtain dabigatran etexilate of Formula (F); and
(g) reacting dabigatran etexilate of Formula (F) with methane sulfonic acid in suitable organic solvent to obtain dabigatran etexilate mesylate of Formula (I).

The process embodiments for the preparation of dabigatran etexilate mesylate of Formula (I) are as described herein above for the intermediates steps as well as those described in examples herein after.

The dabigatran etexilate mesylate of Formula (I) prepared by the process of present invention using crystalline intermediates (2A), (2B) and (E) is crystalline Form-I substantially free from crystalline Form-II of dabigatran etexilate mesylate.

The term "substantially free" herein means dabigatran etexilate mesylate crystalline Form-I having about 0.5% or less of crystalline Form-II. In particular, dabigatran etexilate mesylate crystalline Form-I having about 0.1% or less of crystalline Form-II. More particular, dabigatran etexilate mesylate crystalline Form-I having not in detectable amount of crystalline Form-II, when measured by x-ray powder diffraction instrument.

Powder X-ray diffraction of crystalline intermediates and dabigatran etexilate mesylate of Formula (I) may be obtained under following conditions.

Instrument: X-Ray Diffractometer, D/Max-2200/PC Make: Rigaku, Japan.

X-ray: Cu/40 kv/40 mA

Diverging: 10

Scattering Slit: 10

Receiving Slit: 0.15 mm

Monochromator RS: 0.8 mm

Counter: Scintillation Counter

Scan Mode: Continuous

Scan Speed: 3.0000/Min

Sampling Width: 0.020

Scan Axes: Two Theta/Theta

Scan Range: 2.0000 to 40.0000

Theta Offset: 0.00000

In another general aspect, the present invention provides amorphous dabigatran etexilate of Formula (F) and process for its preparation.

In another general aspect, the invention provides amorphous form of dabigatran etexilate of Formula (F)

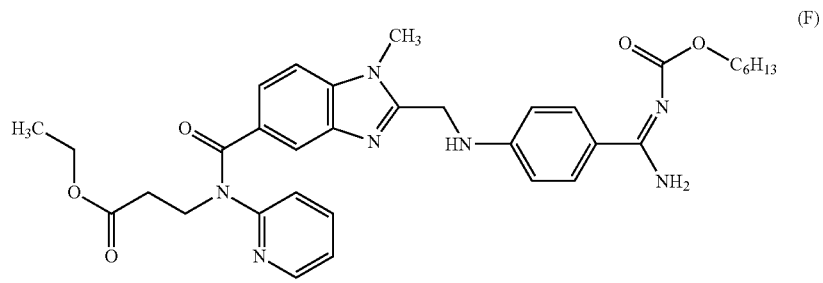

The amorphous form of dabigatran etexilate of Formula (F) has been characterized by X-Ray diffraction pattern as depicted in FIG. 4. An amorphous form of dabigatran etexilate of Formula (F) may be prepared by the process disclosed in U.S. Pat. No. 6,087,380, which is incorporated herein as reference.

In another general aspect, the invention provides substantially pure dabigatran etexilate mesylate of Formula (I). The term "substantially pure" herein means dabigatran etexilate mesylate having a total purity of about 99% or more, particularly about 99.5% or more, more particularly about 99.9% or more, when measured by area percentage of HPLC.

In another general aspect, the present invention provides crystalline Form-I of dabigatran etexilate mesylate having particle size distribution with about 90% of particles being ≤200 μm (microns); 50% of particles (D50) being ≤150 microns; 10% of particles (D10) being ≤100 microns or any combination thereof. In particular, the crystalline Form-I of dabigatran etexilate mesylate having particle size distribution with about 90% of particles being ≤50 μm (microns); 50% of particles (D50) being ≤20 microns; 10% of particles (D10) being ≤10 microns or any combination thereof.

In another general aspect, crystalline Form-I of dabigatran etexilate mesylate may be milled to reduce the particle size and achieve the fine particle size.

In another general aspect, dabigatran etexilate mesylate may be prepared by the reaction scheme-1 as shown below, which is also the scope of the present invention.

SCHEME-1

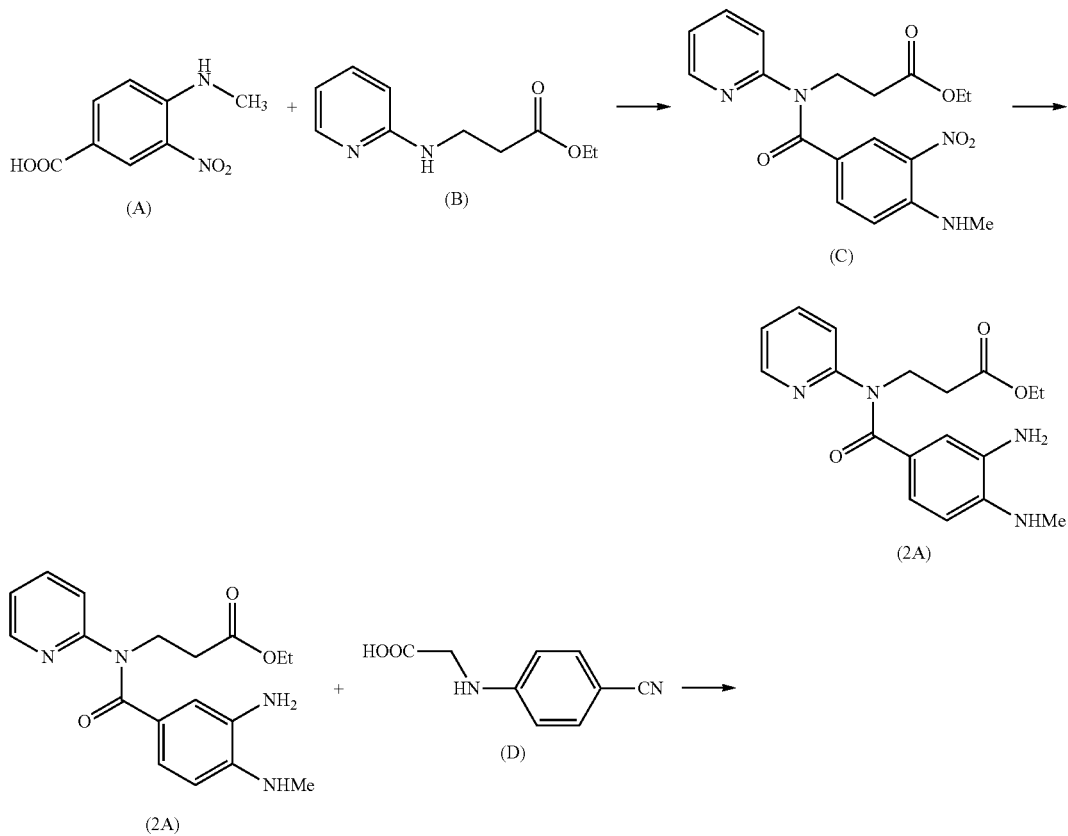

-continued

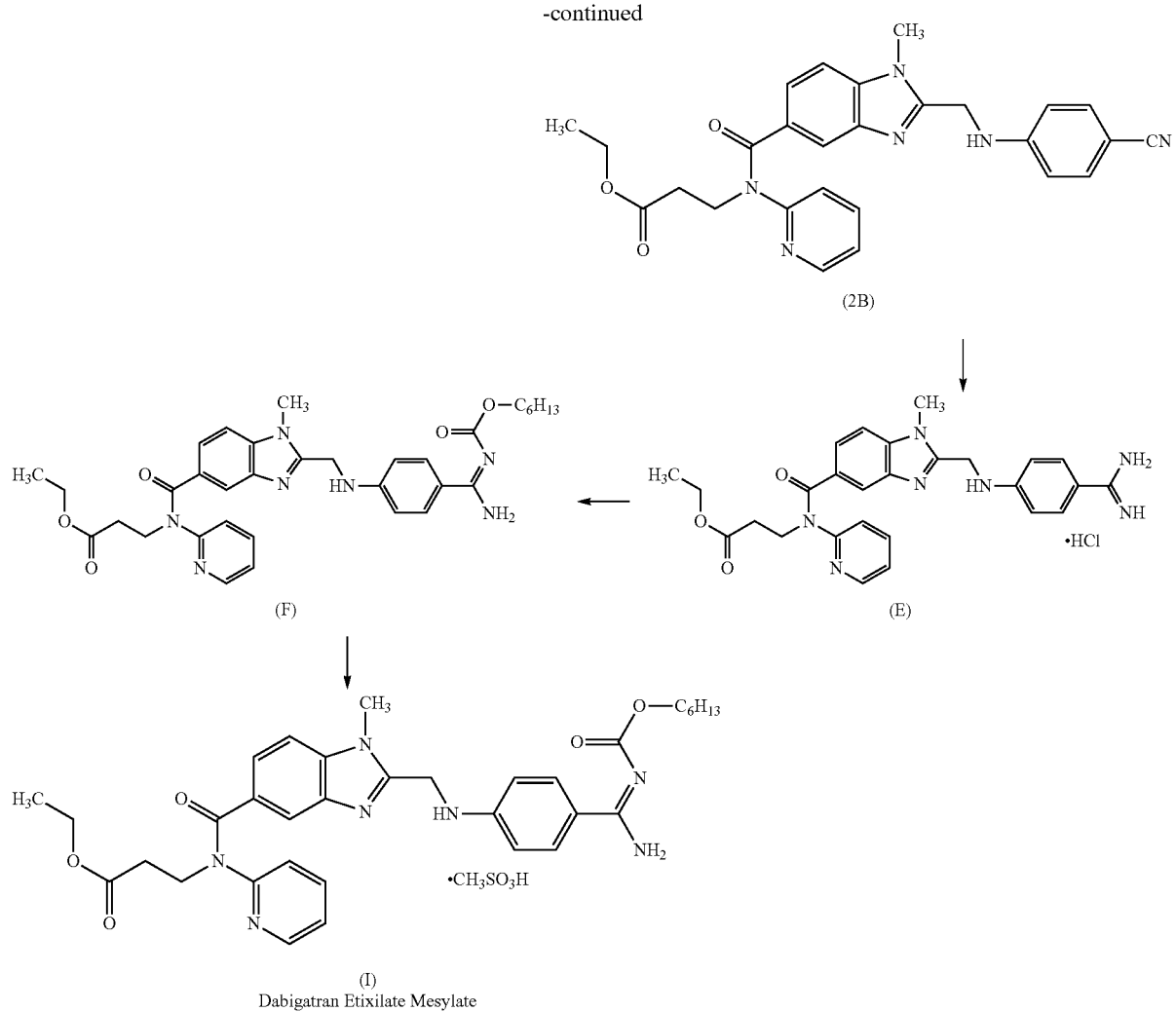

(2B)

(F)

(E)

(I)
Dabigatran Etixilate Mesylate

In another general aspect, there is provided a pharmaceutical compositions comprising therapeutically effective amount of crystalline Form-I of dabigatran etexilate mesylate substantially free from crystalline Form-II, and one or more pharmaceutically acceptable carriers, excipients or diluents.

The invention also encompasses a pharmaceutical compositions comprising crystalline Form-I of dabigatran etexilate mesylate substantially free from Form-II. As used herein, the term "pharmaceutical compositions" includes tablets, pills, powders, liquids, suspensions, emulsions, granules, capsules, suppositories, or injection preparations.

Pharmaceutical compositions containing the crystalline Form-I of dabigatran etexilate mesylate of the present invention may be prepared by using diluents or excipient such as fillers, bulking agents, binders, wetting agents, disintegrating agents, surface active agents and lubricants. Various modes of administration of the pharmaceutical composition of the invention can be selected depending on the therapeutic purpose, for example tablets, pills, powders, liquids, suspensions, emulsions, granules, capsules, suppositories, or injection preparations.

Having described the invention with reference to certain preferred embodiments, other embodiments will become apparent to one skilled in the art from consideration of the specification.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Example-1

Preparation of 4-(methylamino)-3-nitrobenzoic acid of Formula (A)

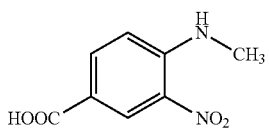

500 g of 4-chloro-3-nitrobenzoic acid and 2 L of mono methyl amine were added stirred for 10-15 minutes at 25° C. to 35° C. The reaction mixture was heated to 55° C. and maintained for 12 hours. The reaction mixture was dumped in ice-water and stirred for 15 minutes and pH was adjusted to 2 by conc. HCl. The reaction mixture was stirred for 15 minutes and filtered. The wet-cake was washed with water and dried to obtain 4-(methylamino)-3-nitrobenzoic acid of Formula (A).

Example-2

Preparation of crystalline ethyl 3-(3-amino-4-(methylamino)-N-(pyridin-2-yl)benzamido) propanoate of Formula (2A)

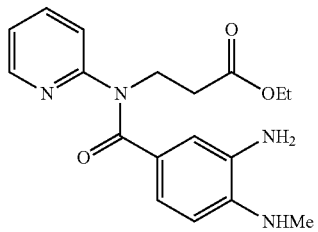 [SMILES: CCOC(=O)CCN(C(=O)c1ccc(NC)c(N)c1)c1ccccn1]

113.6 g of 4-(methylamino)-3-nitrobenzoic acid of Formula (A), 1.2 mL dimethylformamide and thionyl chloride (170.5 mL) were stirred for 15 minutes at 25° C. to 35° C. The reaction mixture was heated to 75° C. to 80° C. for one hour. Excess of thionyl chloride was distilled out. 75 g of ethyl 3-(pyridin-2-ylamino)\propanoate of Formula (B) and ethyl acetate (100 mL) were added to the reaction mixture. 121 mL of triethylamine was added and the reaction mixture was stirred for 1 hour. The reaction mixture was washed with mixture of water and ethyl acetate and charcoalized. The reaction mixture was filtered to obtain of ethyl 3-(4-(methylamino)-3-nitro-N-(pyridin-2-yl)benzamido)propanoate of Formula (C). The compound (C) in-situ in ethyl acetate layer was added 3.75 g Pd/C at 25° C. to 35° C. and stirred for 20 min. The reaction mixture was maintained under 5 Kg pressure at 50° C. to 55° C. The reaction mixture was filtered and washed with ethyl acetate and distilled to obtain residue. 150 mL isopropanol was added and heated for 5-10 minutes at 70° C. to 75° C. The reaction mixture was cooled to 0° C. to 5° C. and filtered. The wet-cake was washed with isopropanol and dried to afforded 75% ethyl 3-(3-amino-4-(methylamino)-N-(pyridin-2-yl)benzamido)propanoate of Formula (2A) with 98% purity. The compound of Formula (2A) is characterized by x-ray powder diffraction as depicted in FIG. 1.

Example-3

Preparation of 2-(4-cyanophenylamino) acetic acid of Formula (D)

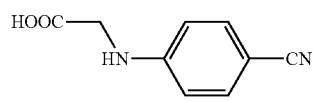 [SMILES: N#Cc1ccc(NCC(=O)O)cc1]

100 g 4-Aminobenzonitrile and 234.7 g bromoacetic acid in 1400 mL water were stirred for 15 min in round bottom flask. The reaction mixture was heated to 100° C. and maintained for 16 hours. The reaction mixture was cooled to 10° C. and stirred for 2 hours. The reaction mixture was filtered and washed with water to obtain 2-(4-cyanophenylamino) acetic acid of Formula (D).

Example-4

Process for preparation of the crystalline ethyl 3-(2-((4-cyanophenylamino)methyl)-1-methyl-N-(pyridin-2-yl)-1H-benzo[d]imidazole-5-carboxamido) propanoate of Formula (2B)

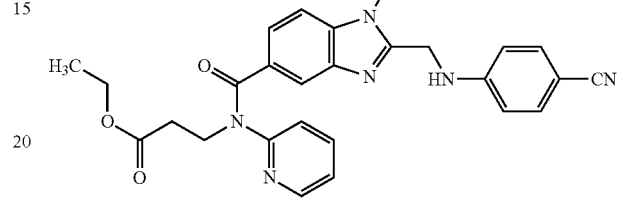

77 g 2-(4-cyanophenylamino) acetic acid of Formula (E), 71.04 g CDI in 1000 mL Toluene were stirred at 25° C. to 35° C. The reaction mixture was heated to 55° C. to 60° C. and maintained for 2 hours. 100 g ethyl 3-(3-amino-4-(methylamino)-N-(pyridin-2-yl)benzamido)propanoate of Formula (2A) was added to the reaction mixture and stirred for 3 hours at 60° C. to 65° C. The reaction mixture was further heated at 100° C. for 3 hours. Toluene was distilled under vacuum. The residue was treated with 500 mL methylene dichloride and organic layer was washed with water. The organic layer was filtered and washed with methylene dichloride. The methylene dichloride was distilled under vacuum and 100 mL ethyl acetate was added at 40° C. to 45° C. and stirred for 15 minutes. The reaction mixture was heated to 75° C. and cooled to 10° C. to 15° C. The reaction mixture was stirred for 2 hours and the precipitated product was filtered and washed with 150 mL ethyl acetate to obtain crystalline ethyl 3-(2-((4-cyanophenylamino)methyl)-1-methyl-N-(pyridin-2-yl)-1H-benzo[d]imidazole-5-carboxamido) propanoate of Formula (2B). The compound of Formula (2B) is characterized by x-ray powder diffraction as depicted in FIG. 2.

Example-5

Preparation of crystalline ethyl 3-(2-((4-carbamimidoylphenylamino)methyl)-1-methyl-N-(pyridin-2-yl)-1H-benzo[d]imidazole-5-carboxamido)propanoate hydrochloride of Formula (E)

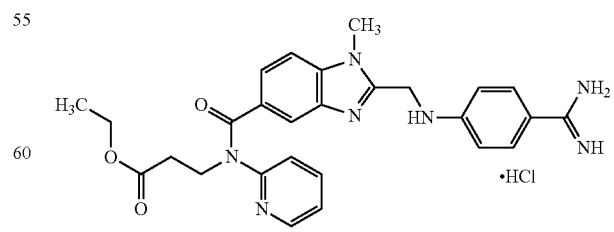

120 mL ethanol was cooled to 0° C. to 5° C. in round bottom flask and HCl gas was purged till HCl content was 30%. 20 g ethyl 3-(2-((4-cyanophenylamino)methyl)-1-methyl-N-(pyridin-2-yl)-1H-benzo[d]imidazole-5-carboxamido) propanoate of Formula (2B) was added and the reaction mixture was heated to 25° C. to 35° C. Ethanol was distilled under vacuum and the residue was treated with 150 mL t-butanol and stirred for 2 hours. The reaction mixture was filtered and washed with 20 mL mixture of t-butanol to obtain ethyl 3-(2-((4-carbamimidoylphenylamino)methyl)-1-methyl-N-(pyridin-2-yl)-1H-benzo[d]imidazole-5-carboxamido)propanoate hydrochloride of Formula (E). The compound of Formula (E) was recrystallized in t-butanol to obtain crystalline compound of Formula (E) characterized by x-ray powder diffraction pattern as depicted in FIG. 3.

Example-6

Process of Preparation of Dabigatran Etexilate of Formula (F)

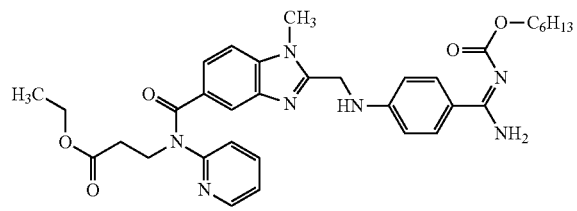

350 mL acetone, 250 mL water and 32.2 g potassium carbonate were stirred in round bottom flask at 25° C. The reaction mixture was cooled to 10° C. and 100 g of 1-methyl-2-[N-(4-amidinophenyl)aminomethyl]benzimidazol-5-yl-carboxylic acid-N-phenyl-N-(2-ethoxy carbonylethyl)amide hydrochloride of Formula (E) was added. 15 mL acetone and 16.8 mL n-hexyl chloroformate were added to the reaction mixture and stirred for 1 hour. The precipitated product was filtered and washed with mixture of acetone and water. The wet-cake was dissolved in acetone and stirred for 30 min. The product was obtained by addition of water followed by filtration. The wet-cake thus obtained was washed with acetone and dried to obtain dabigatran etexilate of Formula (E). 50 g dabigatran etexilate and 500 mL ethyl acetate were stirred at 25° C. The reaction mixture was charcoalized and filtered. The filtrate was heated 75° C. to 80° C. and stirred for 30 minutes and cooled to 25° C. to 35° C. The reaction mixture was filtered and washed with ethyl acetate to obtain pure dabigatran etexilate of Formula (F).

Example-7

Preparation of Amorphous Form of Dabigatran Etexilate of Formula (F) as per U.S. Pat. No. 6,087,380

73 gm ethyl 3-(2-((4-carbamimidoylphenylamino)methyl)-1-methyl-N-(pyridin-2-yl)-1H-benzo[d]imidazole-5-carboxamido)propanoate hydrochloride of Formula (E) in 1460 mL methylene dichloride were stirred 25° C. to 35° C. and cooled to 0° C. to 5° C. To the reaction mixture was treated with 61.1 mL triethylamine at 0° C. to 5° C. and stirred for 30 minutes followed by addition of n-hexyl chloroformate solution (31.35 mL in 365 mL methylene dichloride for 2 hrs. The residue was treated with 730 mL water and extracted with 370 mL methylene dichloride. The methylene dichloride was distilled and the residue was purified using mixture of methylene dichloride and ethanol to afforded amorphous form of dabigatran Etexilate of Formula (F). The amorphous form of dabigatran etexilate of Formula (F) is characterized by x-ray powder diffraction pattern as depicted in FIG. 4.

Example-8

Process of Preparation of Form-I of Dabigatran Etexilate Mesylate of Formula (I)

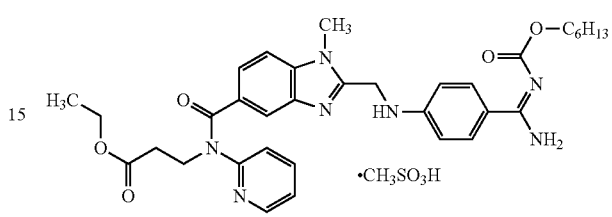

30 g of dabigatran etexilate 30 g was dissolved in 780 mL acetone and stirred for 20 min at 25-30° C. The reaction mixture was treated with charcoal and filtered. The wet-cake was washed with acetone. The filtrate was treated with 2.79 mL solution of methane sulfonic acid in 300 mL acetone. The reaction mixture was stirred for 2 hours at 25° C. to 30° C. and filtered. The wet-cake was slurried in acetone at 25° C. to 30° C. and filtered. The wet-cake was washed with acetone and dried to obtain dabigatran etexilate mesylate crystalline Form-I of Formula (I) characterized by x-ray powder diffraction pattern as depicted in FIG. 5. PSD distribution (D(90) =35.74 µm, D(50)=10.16 µm and D(10)=2.50 µm). Form-II is below detection limit.

While the present invention has been described in terms of its specific embodiments, certain modifications and equivalents will be apparent to those skilled in the art and are intended to be included within the scope of the present invention.

We claim:

1. A process for preparation of dabigatran etexilate of Formula (F)

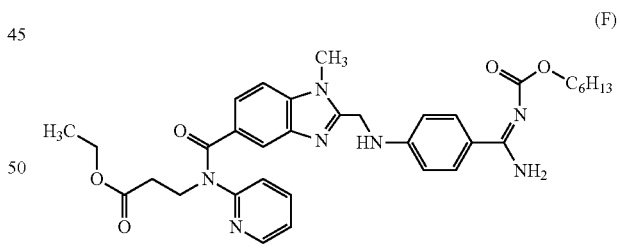

or a pharmaceutically acceptable salt thereof,
the process comprising the steps of:
(a) treating crystalline ethyl 3-(2-((4-cyanophenylamino)methyl)-1-methyl-N-(pyridin-2-yl)-1H-benzo[d]imidazole-5-carboxamido)propanoate of Formula (2B) with an acid in organic solvent to obtain a reaction mixture;
(b) basifying the reaction mixture followed by removal of solvent to obtain a residue;
(c) crystallizing the residue in an organic solvent to obtain crystalline 1-methyl-2-[N-(4-amidinophenyl)aminomethyl]benzimidazol-5-yl-carboxylic acid-N-phenyl-N-(2-ethoxy carbonylethyl)amide hydrochloride of Formula (E);

(d) reacting crystalline 1-methyl-2-[N-(4-amidinophenyl) aminomethyl]benzimidazol-5-yl-carboxylic acid-N-phenyl-N-(2-ethoxycarbonylethyl)amide hydrochloride of Formula (E) with n-hexyl chloroformate in presence of base in organic solvent to obtain dabigatran etexilate of Formula (F);

(e) crystallizing dabigatran etexilate in an organic solvent;

(f) obtaining substantially pure dabigatran etexilate of Formula (F) by removal of solvent; and (g) optionally, converting dabigatran etexilate of Formula (F) to a pharmaceutically acceptable salt thereof.

2. The process as claimed in claim 1, wherein crystalline ethyl 3-(2-((4-cyanophenylamino)methyl)-1-methyl-N-(pyridin-2-yl)-1H-benzo[d]imidazole-5-carboxamido)propanoate of Formula (2B) is characterized by an X-ray diffraction pattern that exhibits characteristic peaks at about 5.8°, 11.7°, 11.9°, 13.5°, 16.6°, 17.6°, 18.8°, 19.3°, 21.1°, 24.2°, 25.5°, 25.9°, and 27.5°2θ±0.2.

3. The process as claimed in claim 1, wherein the crystalline form of ethyl 3-(2-((4-cyano phenyl amino)methyl)-1-methyl-N-(pyridin-2-yl)-1H-benzo[d]imidazole-5-carboxamido) propanoate of Formula (2B) is characterized by X-ray diffraction pattern substantially as depicted in FIG. 2.

4. The process as claimed in step (a) of claim 1, wherein the acid is selected from organic or inorganic acid selected from formic acid, acetic acid, trifluoroacetic acid, hydrochloric acid, hydrobromic acid, sulfuric acid and phosphoric acid.

5. The process as claimed in claim 4 wherein the acid is hydrochloric acid.

6. The process as claimed in step (a) of claim 1 wherein the organic solvent comprises one or more of methanol, ethanol, isopropanol, n-butanol, t-butanol, acetone, methyl ethyl ketone, diethyl ether, diisopropyl ether, methyl tert-butyl ether, ethyl acetate, isopropyl acetate, butyl acetate, dimethylformamide, dimethylacetamide, N-methylpyrrolidine, toluene, xylene, acetonitrile or a mixture thereof.

7. The process as claimed in claim 1, wherein a base for basification is selected from ammonia, ammonium carbonate and ammonical solution in alcohol wherein the alcohol is selected from methanol, ethanol, isopropanol and butanol.

8. The process as claimed in claim 1, wherein the solvent for crystallization comprises one or more of methanol, ethanol, isopropanol, n-butanol, t-butanol, acetone, methyl ethyl ketone, diethyl ether, diisopropyl ether, methyl tert-butyl ether, ethyl acetate, isopropyl acetate, butyl acetate, dimethyl formamide, dimethylacetamide, N-methylpyrrolidine, toluene, xylene, and acetonitrile or a mixture thereof.

9. The process as claimed in claim 1, wherein crystalline 1-methyl-2-[N-(4-amidinophenyl)amino methyl]benzimidazol-5-yl-carboxylic acid-N-phenyl-N-(2-ethoxy carbonyl ethyl)amide hydrochloride of Formula (E) is characterized by X-ray diffraction pattern that exhibits the characteristic peaks at about 7.1°, 7.7°, 9.7°, 12.0°, 13.5°, 14.3°, 15.4°, 17.2°, 19.2°, 20.4°, 21.5°, 22.3°, 23.9°, 24.3°, 25.4°, 26.5°, 27.4°, and 28.8°2θ±0.2.

10. The process as claimed in claim 1, wherein crystalline form of 1-methyl-2-[N-(4-amidophenyl)amino methyl]benzimidazol-5-yl-carboxylic acid-N-phenyl-N-(2-ethoxycarbonyl)amide hydrochloride of Formula (E) is characterized by X-ray diffraction pattern substantially as depicted in FIG. 3.

11. The process as claimed in step (d) of claim 1, wherein the base is selected from alkali or alkaline earth metal salts selected from sodium hydroxide, potassium hydroxide, lithium hydroxide, calcium hydroxide, sodium carbonate, potassium carbonate, sodium bicarbonate, potassium bicarbonate, sodium tert-butoxide and potassium tert-butoxide.

12. The process as claimed in step (d) of claim 1, wherein the organic solvent comprises of one or more of methanol, ethanol, isopropanol, n-butanol, t-butanol, acetone, methyl ethyl ketone, ethyl acetate, isopropyl acetate, butyl acetate, dimethylformamide, dimethyl acetamide, N-methylpyrrolidine, dimethylsulfoxide, toluene, xylene, and acetonitrile or a mixture thereof with water.

13. The process as claimed in claim 1, wherein the organic solvent for crystallization of dabigatran etexilate comprises one or more of methanol, ethanol, isopropanol, n-butanol, t-butanol, acetone, methyl ethyl ketone, ethyl acetate, isopropyl acetate, butyl acetate, dimethylformamide, dimethylacetamide, N-methylpyrrolidine, dimethylsulfoxide, toluene, xylene, acetonitrile or a mixture thereof.

14. The process as claimed in claim 1, wherein the pharmaceutically acceptable salt is selected from hydrochloride, hydrobromide, oxalate, succinate, tartrate, mesylate and besylate.

* * * * *